United States Patent [19]

Robertson et al.

[11] Patent Number: 5,023,269

[45] Date of Patent: Jun. 11, 1991

[54] 3-ARYLOXY-3-SUBSTITUTED PROPANAMINES

[75] Inventors: David W. Robertson, Greenwood; David T. Wong; Joseph H. Krushinski, Jr., both of Indianapolis, all of Ind.

[73] Assignee: Eli Lilly and Company, Indianapolis, Ind.

[21] Appl. No.: 499,940

[22] Filed: Mar. 27, 1990

Related U.S. Application Data

[60] Division of Ser. No. 462,925, Jan. 12, 1990, Pat. No. 4,956,388, which is a continuation of Ser. No. 945,122, Dec. 22, 1986, abandoned.

[51] Int. Cl.$^5$ .................... A61K 31/38; A61K 31/44; C07D 333/16
[52] U.S. Cl. .................... 514/438; 514/357; 514/365; 514/471; 546/334; 548/205; 549/75; 549/491
[58] Field of Search .................. 549/75, 491; 546/334; 548/205; 514/438, 471, 357, 365

[56] References Cited

U.S. PATENT DOCUMENTS

| | | | |
|---|---|---|---|
| 2,842,555 | 7/1958 | Harfenist et al. | 548/574 |
| 3,423,510 | 1/1969 | Sigg | 514/357 |
| 3,433,804 | 3/1969 | Hollinger et al. | 549/59 |
| 3,814,750 | 6/1974 | Cross et al. | 540/596 |
| 4,018,895 | 4/1977 | Molloy et al. | 514/649 |
| 4,194,009 | 3/1980 | Molloy et al. | 514/651 |
| 4,314,081 | 2/1982 | Molloy et al. | 564/347 |
| 4,329,356 | 5/1986 | Holland | 514/419 |
| 4,857,543 | 8/1989 | Hayashi et al. | 549/75 |
| 4,902,710 | 2/1990 | Foster et al. | 514/438 |

FOREIGN PATENT DOCUMENTS

| | | |
|---|---|---|
| 2482956 | 5/1980 | France . |
| 1343527 | 1/1974 | United Kingdom . |
| 2060618 | 5/1981 | United Kingdom . |

*Primary Examiner*—Mary C. Lee
*Assistant Examiner*—Lenora Miltenberger
*Attorney, Agent, or Firm*—Robert A. Conrad; Leroy Whitaker

[57] ABSTRACT

The present invention provides 3-aryloxy-3-substituted propanamines capable of inhibiting the uptake of serotonin and norepinephrine.

51 Claims, No Drawings

3-ARYLOXY-3-SUBSTITUTED PROPANAMINES

This application is a division of application Ser. No. 07/462,925, filed Jan. 12, 1990, now U.S. Pat. No. 4,956,388, continuation of application Ser. No. 06/945,122, filed on Dec. 22, 1986, now abandoned.

BACKGROUND OF THE INVENTION

During the past decade, the relationship between monoamine uptake and a variety of diseases and conditions has been appreciated and investigated. For example, the hydrochloride salt of fluoxetine (dl-N-methyl-γ-[4-(trifluoromethyl)phenoxy]benzenepropanamine) is a selective serotonin (5-hydroxytryptamine) uptake inhibitor presently undergoing clinical evaluation for the treatment of depression, anxiety, appetite suppression, and other disorders. Similarly, tomoxetine hydrochloride ((−)-N-methyl-δ-(2-methylphenoxy)benzenepropanamine hydrochloride) is a selective inhibitor of norepinephrine uptake being investigated clinically for its antidepressant activity. These compounds are among many taught in U.S. Pat. Nos. 4,018,895, 4,194,009, and 4,314,081 as being potent but selective blockers of the uptake of a particular monoamine.

SUMMARY OF THE INVENTION

The present invention provides novel 3-aryloxy-3-substituted propanamines which are potent inhibitors of both serotonin and norepinephrine uptake. More specifically, the present invention relates to a compound of the formula

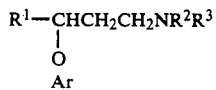

wherein:

$R^1$ is $C_5-C_7$ cycloalkyl, thienyl, halothienyl, ($C_1-C_4$ alkyl)thienyl, furanyl, pyridyl or thiazolyl;

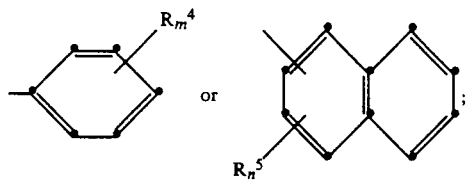

each of $R^2$ and $R^3$ independently is hydrogen or methyl;
each $R^4$ independently is halo, $C_1-C_4$ alkyl, $C_1-C_3$ alkoxy or trifluoromethyl;
each $R^5$ independently is halo, $C_1-C_4$ alkyl or trifluoromethyl;
m is 0, 1 or 2;
n is 0 or 1; and
the pharmaceutically acceptable acid addition salts thereof.

The invention also provides pharmaceutical formulations comprising a compound of the above formula and a pharmaceutically acceptable carrier, diluent or excipient therefor.

A further embodiment of the invention are methods for selectively inhibiting the uptake of serotonin and norepinephrine, as well as for treating a variety of disorders which have been linked to decreased neurotransmission of serotonin and norepinephrine in mammals including obesity, depression, alcoholism, pain, loss of memory, anxiety, smoking, and the like, employing a compound of the invention.

DETAILED DESCRIPTION OF THE INVENTION

In the above formula, the term $C_1-C_4$ alkyl represents a straight or branched alkyl chain bearing from one to four carbon atoms. Typical $C_1-C_4$ alkyl groups include methyl, ethyl, n-propyl, isopropyl, n-butyl, isobutyl, sec.-butyl and t-butyl.

$C_1-C_3$ Alkoxy represents methoxy, ethoxy, n-propoxy or isopropoxy.

Halo represents fluoro, chloro, bromo or iodo.

When Ar is naphthalenyl, it can be either 1-naphthalenyl or 2-naphthalenyl.

When $R^1$ is thienyl, it can be either 2-thienyl or 3-thienyl; when $R^1$ is furanyl, it can be either 2-furanyl or 3-furanyl; when R' is pyridyl, it can be either 2-pyridyl, 3-pyridyl or 4-pyridyl; when $R^1$ is thiazolyl, it can be either 2-thiazolyl, 4-thiazolyl or 5-thiazolyl.

($C_1-C_4$ Alkyl)thienyl represents a thienyl ring monosubstituted with a $C_1-C_4$ alkyl substituent. Typical $C_1-C_4$ alkyl)thienyl groups include 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2thienyl, and the like.

Halothienyl represents a thienyl ring monosubstituted with a halo substituent. Typical halo-thienyl groups include 3-chloro-2-thienyl, 4-bromo-3-thienyl, 2-iodo-3-thienyl, 5-iodo-3-thienyl, 4-fluoro-2-thienyl, 2-bromo-3-thienyl, 4-chloro-2-thienyl and the like.

While all of the compounds of the present invention are believed to inhibit the uptake of serotonin and norepinephrine in mammals, there are certain of these compounds which are preferred for such uses. Preferably, $R^1$ is halothienyl, ($C_1-C_4$ alkyl)thienyl and especially thienyl. Further, one of $R^2$ and $R^3$ is hydrogen and the other is methyl. It is also preferred that those compounds wherein both $R^2$ and $R^3$ are other than methyl are preferred for inhibiting the uptake of norepinephrine in mammals. Other preferred aspects of the present invention will be noted hereinafter.

The compounds of the present invention possess an asymmetric carbon represented by the carbon atom labeled "C" in the following formula:

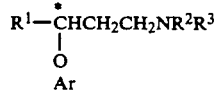

As such, the compounds can exist as the individual stereoisomers as well as the racemic mixture. Accordingly, the compounds of the present invention will include not only the dl-racemates, but also their respective optically active d- and l-isomers.

As pointed out above, the invention includes the pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate and the like salts. Preferred pharmaceutically aoceptable acid addition salts include those formed with mineral acids such as hydrochloric acid and hydrobromic acid, and especially those formed with organic acids such oxalic acid and maleic acid.

The following compounds further illustrate compounds contemplated within the scope of the present invention:

N-Methyl-3-(1-naphthalenyloxy)-3-(3-thienyl)-propanamine phosphate
N-Methyl-3-(2-naphthalenyloxy)-3-(cyclohexyl)-propanamine citrate
N,N-Dimethyl-3-(4-chloro-1-naphthalenyloxy)-3-(3-furanyl)propanamine hydrochloride
N-Methyl-3-(5-methyl-2-naphthalenyloxy)-3-(2-thiazolyl)propanamine hydrobromide
N-Methyl-3-[3-(trifluoromethyl)-1-naphthalemyloxy]-3-(3-methyl-2-thienyl)propanamine oxalate
N-Methyl-3-(6-iodo-1-naphthalenyloxy)-3-(4-pyridyl)-propanamine maleate
N,N-Dimethyl-3-(1-naphthalenyloxy)-3-(cycloheptyl)-propanamine formate
N,N-Dimethyl-3-(2-naphthalenyloxy)-3-(2-pyridyl)-propanamine
N-Methyl-3-(1-naphthalenyloxy)-3-(2-furanyl)propanamine sulfate
N-Methyl-3-(4-met naphthalenyloxy)-3-(4-thiazolyl)-propanamine oxalate
N-Methyl-3-(2-naphthalenyloxy)-3-(2-thienyl)propanamine hydrochloride
N,N-Dimethyl-3-6-iodo-2-naphthalenyloxy)-3-(4-bromo-3-thienyl)propanamine malonate
N,N-Dimethyl-3-(1-naphthalenyloxy)-3-(3-pyridyl)-propanamine hydroiodide
N,N-Dimethyl-3-(4-methyl-2-naphthalenyloxy)-3-(3-furanyl)propanamine maleate
N-Methyl-3-(2-naphthalenyloxy)-3-(cyclohexyl)-propanamine caprate
N-Methyl-3-(6-n-propyl-1-naphthalenyloxy)-3-(3-isopropyl-2-thienyl)propanamine citrate
N,N-Dimethyl-3-(2-methyl-1-naphthalenyloxy)-3-(4-thiazolyl)propanamine monohydrogen phosphate
3-(1-Naphthalenyloxy)-3-(5-ethyl-3-thienyl)propanamine succinate
3-3-(Trifluoromethyl)-1-naphthalenyloxy]-3-(pyridyl)-propanamine acetate
N-Methyl-3-(6-methyl-1-naphthalenyl-3-(4-chloro-2-thienyl)propanamine tartrate
3-(2-Naphthalenyloxy)-3-(cyclopentyl)propanamine
N-Methyl-3-(4-n-butyl-1-naphthalenyloxy)-3-(3-furanyl)propanamine methanesulfonate
3-(2-Chloro-1-naphthalenyloxy)-3-(5-thiazolyl)-propanamine oxalate
N-Methyl-3-(1-naphthalenyloxy)-3-(3-furanyl)propanamine tartrate
N,N-Dimethyl-3-(phenoxy)-3-(2-furanyl)propanamine oxalate
N,N-Dimethyl-3-[4-(trifluoromethyl)phenoxy]-3-(cyclohexyl)propanamine hydrochloride
N-Methyl-3-(4-methylphenoxy)-3-(4-chloro-2-thienyl)-propanamine propionate
N-Methyl-3-(phenoxy)-3-(3-pyridyl)propanamine oxalate
3-[2-Chloro-4-(trifluoromethyl)phenoxy]-3-(2-thienyl)-propanamine
N,N-Dimethyl-3-(3-methoxyphenoxy)-3-(3-bromo-2-thienyl)propanamine citrate
N-Methyl-3-(4-bromophenoxy)-3-(4-thiazolyl)propanamine maleate
N,N-Dimethyl-3-(2-ethylphenoxy)-3-(5-methyl-3thienyl)propanamine
N-Methyl-3-(2-bromophenoxy)-3-(3-thienyl)propanamine succinate
N-Methyl-3-(2,6-dimethylphenoxy)-3-(3-methyl-2-thienyl)propanamine acetate
3-[3-(Trifluoromethyl)phenoxy]-3-(3-furanyl)propanamine oxalate
N-Methyl-3-(2,5-dichlorophenoxy)-3-(cyclopentyl)-propanamine
3-4-(Trifluoromethyl)phenoxy]-3-(2-thiazolyl)propanamine
N-Methyl-3-(phenoxy)-3-(5-methyl-2-thienyl)propanamine citrate
3-(4-Methylphenoxy)-3-(4-pyridyl)propanamine hydrochloride
N,N-Dimethyl-3-(3-methyl-5-bromophenoxy)-3-(3-thienyl)propanamine
N-Methyl-3-(3-n-propylphenoxy)-3-(2-thienyl)propanamine hydrochloride
N-Methyl-3-(phenoxy)-3-(3-thienyl)propanamine phosphate
N-Methyl-3-(4-methoxyphenoxy)-3-(cycloheptyl) propanamine citrate
3-(2-Chlorophenoxy)-3-(5-thiazolyl)propanamine propionate
3-2-Chloro-4-(trifluoromethyl)phenoxy]-3-(3-thienyl)-propanamine oxalate
3-(Phenoxy)-3-(4-methyl-2-thienyl)propanamine
N,N-Dimethyl-3-(4-ethylphenoxy)-3-(3-pyridyl)-propanamine maleate
N,N-Dimethyl-3-[4-(trifluoromethyl)phenoxy]-3-(2-pyridyl)propanamine The compounds of the present invention may be prepared by procedures well known to those of ordinary skill in the art. The compounds are preferably synthesized by treating an hydroxy intermediate with an alkali metal hydride to form the corresponding alkali metal salt, which is then reacted with an appropriate compound containing a good leaving group to provide the corresponding 3-aryloxy-3-substituted propanamine of the invention. This reaction may be represented by the following scheme:

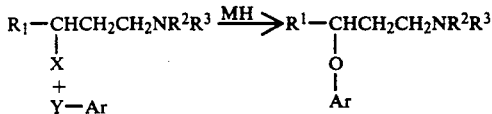

wherein M is an alkali metal, $R^1$, $R^2$, $R^3$ and Ar are as defined above, and one of X and Y is hydroxy and the other is a good leaving group such as p-toluenesulfonyl, methanesulfonyl, triphenylphosphine oxide, halo and the like. Preferably X is hydroxy and Y is halo.

This reaction is carried out by combining approximately equimolar quantities to a slight excess of the alkali metal hydride with the alcohol to provide the corresponding alkali metal salt. Typical alkali metal hydrides include sodium hydride and potassium hydride. The compound is then reacted with an equimolar quantity to slight excess of the compound having the good leaving group. The reaction is conducted in a suitable aprotic solvent such as N,N-dimethylacetamide and related solvents. The reaction is substantially complete after about 10 minutes to about 24 hours when conducted at a temperature in the range of about 25° C. to about 150° C. More preferably, the reaction mixture will be complete within about 30 minutes to about 6 hours when conducted at a temperature in the range of about 75° C. to about 125° C. The product may be isolated by standard conditions as well. Typically, the mixture is diluted with water and extracted with a water immiscible organic solvent such as diethyl ether, ethyl acetate, chloroform and the like. The organic extracts are typically combined and dried. Following evaporation of the organic solvent the isolated residue may be further purified, if desired, by standard techniques such as crystallization from common solvents, or chromatography over solid supports such as silica gel or alumina.

The compounds of the present invention wherein one of $R^2$ and $R^3$ is hydrogen and the other is methyl are preferably prepared by demethylating the corresponding N,N-dimethylpropanamine. Preferably, a reagent such a phenyl chloroformate or trichloroethyl chloroformate is reacted with the N,N-dimethylpropanamine to provide the corresponding intermediate, which is then hydrolyzed in base to provide the corresponding N-methylpropanamine.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and the like.

The compounds employed as starting materials in the synthesis of the compounds of the invention are also prepared by standard procedures. Preferably, standard Mannich reaction conditions are employed to synthesize the corresponding Mannich Base from the appropriate ketone, formaldehyde and dimethylamine, which is then reduced with a hydride reducing agent, such as sodium brohydride, employing standard reduction conditions. The analogs containing the leaving group are also prepared by known procedures or are commercially available from various organic laboratories.

The pharmaceutically acceptable acid addition salts of the invention are typically formed by reacting a 3-aryloxy-3-substituted propanamine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

N,N-Dimethyl-3-(1-naphthalenyloxy)-3-(2-thienyl)-propanamine oxalate

A. 3-Dimethylamino-1-(2-thienyl)-1-propanone hydrochloride

A mixture of 2-acetylthiophene (63.1 g, 0.5 mol), dimethylamine hydrochloride (53.0 g, 0.65 mol), paraformaldehyde (19.8 g, 0.22 mol), and 12N hydrochloric acid (1 ml) in ethanol (80 ml) was refluxed for one and one-half hours. The solution was diluted with ethanol (100 ml) and acetone (500 ml). The solution was chilled overnight and the resulting solid was collected by filtration to yield 75.0 g (73%) of 3-dimethylamino-1-(2-thienyl)-1-propanone hydrochloride as a colorless crystalline solid. mp =182° C.-184° C.

Analysis calculated for $C_9H_{14}ClNOS$ Theory: C, 49.20; H, 6.42; N, 6.37; Found: C, 49.40; H, 6.21; N, 6.09.

B. α-[2-(Dimethylamino)ethyl]-2-thiophene methanol

To a solution of 3-dimethylamino-1-(2-thienyl)-1-propanone hydrochloride (70.0 g, 0.34 mol) in 840 ml of methanol and 420 ml of water at about 0° C. was added 5N sodium hydroxide until the solution was slightly basic. To the resulting solution was added sodium borohydride (12.9 g., 0.34 mol) in portions. The mixture was allowed to warm to room temperature overnight. The methanol was removed in vacuo and the remaining solution was diluted with water. The solution was extracted with diethyl ether, and the solution was washed with a saturated sodium chloride solution, dried over anhydrous sodium sulfate and concentrated in vacuo to provide 56.7 g of colorless crystals. Recrystallization of the crystals from hexanes gave 49.24 g (78%) of the title compound as colorless crystals. mp =72° C.-74° C.

Analysis calculated for $C_9H_{19}NOS$ Theory: C, 58.34; H, 8.16; N, 7.56; Found: C, 58.62; H, 8.29; N, 7.68.

C. α-2-(Dimethylamino)ethyl]-2-thiophene methanol (2.0 g, 0.011 mol) was added in portions to a solution of 60% sodium hydride (463 mg, 0.012 mol) in 100 ml of dimethylacetamide. The resulting mixture was heated at 70° C. for 20 minutes. 1-Fluoronaphthalene (1.27 ml, 0.012 m) was added dropwise to the mixture and the resulting solution was heated at 110° C. for 60 minutes. The reaction mixture was diluted with water and extracted twice with diethyl ether. The extracts were combined, washed with water followed by a saturated sodium chloride solution, dried over anhydrous sodium sulfate and concentrated under reduced pressure to yield 3.2 g of an oil. Crystallization of the oil as the oxalate salt from ethyl acetate/methanol yielded 3.28 g (75.6%) of N,N-dimethyl-3-(1-naphthalenyloxy)-3-(2-thienyl)propanamine oxalate as a white solid. mp =148° C.-148.5° C.

Analysis calculated for $C_{21}H_{23}NO_5S$ Theory: C, 62.83; H, 5.77; N, 3.49; Found : C, 62.70; H, 5.88; N, 3.26.

EXAMPLE 2

N-Methyl-3-(1-naphthalenyloxy)-3-(2-thienyl)propanamine oxalate

Phenyl chloroformate (794 μl, 0.0063 mol) was added dropwise to a refluxing solution of N,N-dimethyl-3-(1-naphthalenyloxy)-3-(2-thienyl)propanamine (1.79 g, 0.0058 mol) in 100 ml of toluene. The resulting solution was refluxed one and one half hours and cooled to room temperature. The solution was washed (2.5N sodium hydroxide, water, 1N hydrochloric acid, brine), dried over anhydrous sodium sulfate and concentrated in vacuo to give 2.4 g of the crude carbamate. 5N Sodium hydroxide (11.5 ml, 0.058 mol) was added to a solution of the carbamate (2.4 g, 0.0058 mole) in propylene glycol (100 ml). The mixture was heated at 110° C. for 75 minutes. The reaction mixture was diluted with water and extracted with diethyl ether. The organic phase was washed with water and then a saturated sodium chloride solution, dried over anhydrous sodium sulfate, and concentrated under vacuum to yield 1.5 g of an oil. Crystallization of the oil as the oxalate salt from ethyl acetate/methanol gave 920 mg (41.3%) of the title compound as a white powder. mp =136° C.-138.5° C.

Analysis calculated for $C_{20}H_{21}NO_5S$ Theory: C, 62.00; H, 5.46; N, 3.62; Found: C, 62.21; H, 5.72; N, 3.57.

EXAMPLE 3

N,N-Dimethyl-3-(1-naphthalenyloxy)-3-(5-methyl-2-thienyl)propanamine oxalate

A.

3-Dimethylamino-1-(5-methyl-2-thienyl)-1-propanone hydrochloride

The title compound was prepared according to the general procedure outlined in Example 1 employing 2-acetyl-5-methylthiophene as the starting material to provide 31.3 g (37.4%) of a yellow powder following crystallization from acetone. mp =145° C.-147° C.

Analysis calculated for $C_{10}H_{16}ClNOS$ Theory: C, 51.38; H, 6.90; N, 5.99; Found : C, 51.53; H, 6.82; N, 5.66.

B. α-[2-(Dimethylamino)ethyl]-5-methyl-2thiophene methanol

According to the general procedure set forth in Example 1 using 3-dimethylamino-1-(5-methyl-2-thienyl)-1-propanone hydrochloride as the starting material. The title compound was obtained (50.9%) as an opaque crystalline solid was synthesized. mp =66.5° C.-68° C.

Analysis calculated for $C_{10}H_{17}NOS$ Theory: C, 60.26; H, 8.60; N, 7.03; Found: C, 60.49; H, 8.58; N, 6.91.

C. According to the procedure set forth in Example 1, using α-2-(dimethylamino)ethyl]-5-methyl-2-thiophene methanol as the starting material N,N-dimethyl-3-(1-naphthalenyloxy)-3-(5-methyl-2-thienyl)propanamine was prepared. The crude material was chromatographed over silica gel (eluent-methylene chloride/methanol) to yield 1.4 g (25.5%) of an oil. Crystallization from ethyl acetate/methanol of a small portion of the oil as the oxalate salt gave the title compound as yellow crystals mp =151° C.

Analysis calculated for $C_{22}H_{25}NO_5S$ Theory: C, 63.59; H, 6.06; N, 3.37; Found: C, 63.36; H, 5 84; N, 3.33.

EXAMPLE 4

N,N-Dimethyl-3-(1-naphthalenyloxy)-3-(3-methyl-2-thienyl)propanamine oxalate

A.

3-Dimethylamino-1-(3-methyl-2-thienyl)-1-propanone hydrochloride

The title compound was prepared according to the general procedure set forth in Example 1 using 2-acetyl-3-methylthiophene as the starting material. The crude material was crystallized from acetone to provide 43.4 g (60.7%) of the title compound as a white powder. mp =157° C.-158° C.

Analysis calculated for $C_{10}H_{16}ClNOS$ Theory: C, 51.38; H, 6.90; N, 5.99; Found: C, 51.63; H, 7.14; N, 5.82.

B. α-[2-(Dimethylamino)ethyl]-3-methyl-2-thiophene methanol

The title compound was prepared from 3-dimethylamino-1-(3-methyl-2-thienyl)-1-propanone hydrochloride according to the general procedure of Example 1. Crystallization from hexanes yielded 11.38 g (53.7%) of an opaque crystalline solid. mp =41.5° C.-42.5° C.

Analysis calculated for $C_{10}H_{17}NOS$ Theory: C, 60.26; H, 8.60; N, 7.03; Found: C, 60.80; H, 8.33; N, 6.56.

C. Crude N,N-Dimethyl-3-(1-naphthalenyloxy)-3-(3-methyl-2-thienyl)propanamine, prepared according to the general procedure outlined in Example 1, was chromatographed over silica gel (eluent-methylene chloride/methanol) to yield 10.4 g (74.3%) of an oil. The oil was converted to the oxalate salt and crystallized from ethyl acetate/methanol to give a white powder. mp =140° C.-141° C.

Analysis calculated for $C_{22}H_{25}NO_5S$ Theory: C, 63.59; H, 6.06; N, 3.37; Found: C, 63.85; H, 6.07; N, 3.49.

EXAMPLE 5

N,N-Dimethyl-3-(1-naphthalenyloxy)-3-(5-chloro-2-thienyl)propanamine oxalate

A.

3-Dimethylamino-1-(5-chloro-2-thienyl)-1-propanone hydrochloride

The title compound was prepared according to the general procedure of Example 1 using 2-acetyl-5-chlorothiophene as the starting material. Crystallization from acetone gave 14.55 g (36.9%). mp =170° C.-171° C.

Analysis calculated for $C_9H_{13}Cl_2NOS$ Theory: C, 42.S3; H, 5.16; N, 5.51; Found: C, 42.00; H, 5.23; N, 6.50

B. α-[2-(Dimethylamino)ethyl]-5-chloro-2-thiophene methanol

Three grams of the title compound were prepared from 3-dimethylamino-1-(5-chloro-2-thienyl)-1-propanone hydrochloride according to the general procedure of Example 1 following crystallization from hexanes (38.6%). mp =76° C.-77° C.

Analysis calculated for $C_9H_{14}ClNOS$ Theory: C, 49.20; H, 6.42; N, 6.37; Found: C, 47.37; H, 6.65; N, 6.40.

C. N,N-Dimethyl-3-(1-naphthalenyloxy)-3-(5-chloro-2-thienyl)propanamine was prepared from α2-(dimethylamino)ethyl]-5-chloro-2-thiophene methanol according to the general procedure of Example 1. The crude product was chromatographed over silica gel employing methylene chloride/methanol/ammonium hydroxide as the eluent to yield 320 mg (5.5%) of an oil. Crystallization of the oil as the oxalate salt from ethyl acetate/methanol gave a brown solid. mp = 134° C.-135° C.

Analysis calculated for $C_{21}H_{22}ClNO_5S$ Theory: C, 57.86; H, 5.09; N, 3.21; Found: C, 57.73; H, 5.35; N, 3.30.

EXAMPLE 6

N,N-Dimethyl-3-[4-(trifluoromethyl)-1naphthalenyloxy]-3-(2-thienyl)propanamine oxalate According to the procedure set forth in Example 1 using 4-trifluoromethyl-1-fluoronaphthalene as a starting material, 1.7 g (66.9%) of the title compound as a tan solid was prepared following crystallization from ethyl acetate/methanol. mp = 146° C.-147° C.

Analysis calculated for $C_{22}H_{22}F_3NO_5S$ Theory: C, 56.28; H, 4.72; N, 2.98; Found : C, S6.04; H, 4.65; N, 3.23.

EXAMPLE 7

N-Methyl-3-[4-(trifluoromethyl)-1-naphthalenyloxy]-3-(2-thienyl)propanamine oxalate According to the procedure set forth in Example 2 N,N-dimethyl-3-[4-(trifluoromethyl)-1-naphthalenyloxy]-3-(2-thienyl)propanamine oxalate was converted to the title compound. Crystallization from ethyl acetate/methanol gave 430 mg (33.8%) of a tan powder. mp = 154° C.-156° C.

Analysis calculated for $C_{20}H_{20}F_3NO_5S$ Theory: C, 55.38; H, 4.43; N, 3.08; Found: C, 55.63; H, 4.55; N, 3.27.

EXAMPLE 8

N,N-Dimethyl-3-(1-naphthalenyloxy)-3-(3-thienyl)-propanamine oxalate

A. 3-Dimethylamino-1-(3-thienyl)-1-propanone hydrochloride

The title compound was prepared according to the procedure of Example 1 using 3-acetylthiophene as a starting material. Crystallization from acetone gave 73.9 g (84.9%) of a tan powder. mp = 143° C.-145° C.

Analysis calculated for $C_9H_{14}ClNOS$ Theory: C, 49.20; H, 6.42; N, 6.37; Found: C, 46.27; H, 6.11; N, 7.00.

B. α-[2-(Dimethylamino)ethyl]-3-thiophene methanol

The title compound was prepared according to the procedure in Example 1 using 3-dimethylamino-1-(3-thienyl)-1-propanone hydrochloride as a starting material. Crystallization from diethyl ether/hexane gave 29.0 g (47.7%) of the title compound as a solid. mp = 63° C.-65° C.

Analysis calculated for $C_9H_{15}NOS$ Theory: C, 58.34; H, 8.16; N, 7.56; Found: C, S8.34; H, 8.17; N, 7.72.

C. N,N-Dimethyl-3-(1-naphthalenyloxy)-3-(3-thienyl)propanamine oxalate was prepared according to the procedure of Example 1 using α-[2-(dimethylamino)ethyl]-3-thiophene methanol as a starting material. Crystallization from ethyl acetate/methanol gave 5.88 g (69.8%) of a white powder. mp = 164° C.-165° C.

Analysis calculated for $C_{21}H_{23}NO_5S$ Theory: C, 62.83; H, 5.77; N, 3.49; Found: C, 63.12; H, 6.01; N, 3.51.

EXAMPLE 9

N-Methyl-3-(1-naphthalenyloxy)-3-(3-thienyl)propanamine oxalate

The title compound was prepared according to procedure of Example 2 from N,N-dimethyl-3-(1-naphthalenyloxy)-3-(3-thienyl)propanamine. Crystallization from ethyl acetate/methanol gave 2.97 g (63.6%) of a white powder. mp = 148° C.-150° C.

Analysis calculated for $C_{20}H_{21}NO_5S$ Theory: C, 62.00; H, 5.46; N, 3.62; Found: C, 62.23; H, 5.59; N, 3.85.

EXAMPLE 10

N,N-Dimethyl-3-(4-chloro-1-naphthalenyloxy)-3-(2-thienyl)propanamine oxalate

To a stirred mixture of 4-chloro-1-naphthol (5.36 g, 0.03 mol), α-2-(dimetlylamino)ethyl]-2-thiophene methanol (5.56 g, 0.03 mol), triphenylphosphine (7.87 g, 0.03 mol) and 75 ml of tetrahydrofuran under a nitrogen atmosphere was added 4.8 ml (0.03 mol) of diethylazodicarboxylate dropwise. Occasional cooling was needed to keep the temperature of the reaction mixture below about 30° C. The resulting solution was stirred at room temperature overnight. The volatile constituents were evaporated under vacuum. The residue was diluted with water and the mixture was basified with 5N sodium hydroxide. The mixture was extracted with diethyl ether, and the organic extracts were washed with water and dried over anhydrous sodium sulfate. Evaporation of the diethyl ether and preparative HPLC of the residue using a silica column with a methylene chloride/methanol mixture as eluant yielded 3.7 g (36% yield) of the pure free base as an oil. The oxalate salt was prepared from the above free base by treating an ethyl acetate solution of the free base with oxalic acid. The resulting precipitate was recrystallized from ethanol to afford colorless crystals. mp = 155° C. dec.

Analysis calculated for $C_{21}H_{22}ClNO_5S$ Theory: C, 57.86; H, 5.09; N, 3.21; Found: C, 57.66; H, 4.94; N, 3.12.

EXAMPLE 11

N-Methyl-3-(4-chloro-1-naphthalenyloxy)-3-(2-thienyl)propanamine oxalate

To a stirred solution of N,N-dimethyl-3-(4-chloro-1-naphthalenyloxy)-3-(2-thienyl)propanamine (2.81 g, 8.12 mmol) and 20 ml of toluene heated at 85° C. was added dropwise trichloroethyl chloroformate (1.89 g, 8.93 mmol). The stirring was continued at 85° C. for three hours, and the resulting solution was cooled in an ice bath. To the mixture was added 0.13 ml of 98% formic acid followed by 0.28 ml of triethylamine. The mixture was stirred at room temperature for 30 minutes. The mixture was poured into water and the resulting mixture was extracted with diethyl ether. The organic extracts were washed successively with a saturated sodium chloride solution, a 2N hydrochloric acid solution and a saturated sodium chloride solution. The organic phase was dried over anhydrous sodium sulfate. The volatile constituents were evaporated under vacuum to yield 3.83 g (92% yield) of the crude carbamate as an oil. To a solution of the crude carbamate in 10.0 ml of DMF was added 98% formic acid (0.69 g., 14.9 mmol). The reaction solution was cooled to about 15° C. under a nitrogen atmosphere. Zinc dust (1.22 g, 18.7 mmol) was next added in portions over a 30 minute period. The mixture was stirred at about 15° C. for one hour and then overnight at room temperature. The reaction mixture was filtered through a sintered glass funnel and the filtrate was diluted with water. The acidic solution was made basic with excess cold ammonium hydroxide and then extracted with diethyl ether. The organic extracts were washed with water followed by a saturated sodium chloride solution. The organic phase was dried over anhydrous sodium sulfate and evaporated under vacuum. The residue was purified by preparative HPLC using a silica gel column with a methylene chloride/methanol/ammonium hydroxide (100:5:1, v:v:v) mixture as eluant to give 1.26 g (51% yield) of the free base as an oil.

The oxalate salt was prepared from the free base by treating an ethyl acetate solution of the free base with oxalic acid. The resulting precipitate was crystallized from methanol to afford colorless crystals. mp =182° C. dec.

Analysis calculated for $C_{20}H_{20}ClNO_5S$ Theory: C, 56.94; H, 4.78; N, 3.32; Found: C, 57.22; H, 4.54; N, 3.48.

EXAMPLE 12

N,N-Dimethyl-3-(4-methyl-1-naphthalenyloxy)-3-(2-thienyl)propanamine oxalate

N,N-Dimethyl-3-(4-methyl-1-naphthalenyloxy)-3-(2-thienyl)propanamine oxalate was prepared in 21% yield by the general procedure described in Example 10. The oxalate salt was made and crystallized from ethanol to afford the title compound as colorless crystals. mp =151° C. dec.

Analysis calculated for $C_{22}H_{25}NO_5S$ Theory: C, 63.59: H, 6.06: N, 3.37: Found: C, 63.29: H, 6.02; N, 3.23.

EXAMPLE 13

N-Methyl-3-(4-methyl-1-naphthalenyloxy)-3-(2-thienyl)propanamine maleate

The free base of the title compound was prepared in 44% yield by the procedure described above in Example 11. The maleate salt was prepared from the free base by treating an ethyl acetate solution of the free base with maleic acid. The resulting precipitate was recrystallized from ethanol to afford colorless crystals. mp =174° C. dec.

Analysis calculated for $C_{32}H_{25}NO_5S$ Theory: C, 64.62; H, 5.89; H, 3.28; Found: C, b4.49; H, 5.71; N, 3.48.

The following compounds were prepared according to the general procedures outlined in Examples 1 and 2 above.

EXAMPLE 14

(+)-N-Methyl-3-(1-naphthalenyloxy)-3-(2-thienyl)-propanamine maleate, mp =118° C.-122° C.

$[\alpha]_{589} = +82°$ $[\alpha]_{365} = +391°$ at C=1 in methanol,

Analysis calculated for $C_{22}H_{23}NO_5S$ Theory: C, 63.90; H, 5.61; N, 3.39; S, 7.75; Found: C, 63.78; H, 5.44; N, 3.35; S, 7.64.

EXAMPLE 15

N-Methyl-3-(1-naphthalenyloxy)-3-cyclohexyl-propanamine oxalate, mp =184° C.-185° C.

Analysis calculated for $C_{22}H_{29}NO_5S$ Theory: C, 68.20; H, 7.54; N, 3.61; Found: C, 68.36; H, 7.30; N, 3.45.

EXAMPLE 16

N-Methyl-3-(1-naphthalenyloxy)-3-(2-thiazolyl)-propanamine oxalate, mp =183° C.-185° C.

Analysis calculated for $C_{19}H_{20}N_2O_5S$ Theory: C, 58.75; H, 5.19; N, 7.21; Found: C, 59.02; H, 4.94; N, 7.47.

EXAMPLE 17

N,N-Dimethyl-3-[4-(trifluoromethyl)phenoxy]-3-(2-furanyl)propanamine oxalate, mp =144.5° C.-145.5° C.

Analysis calculated for $C_{18}H_{20}F_3NO_6$ Theory C, 53.60; H, 5.00; N, 3.47; Found: C, 53.83; H, 5.22; N, 3.23.

EXAMPLE 18

N,N-Dimethyl-3-[4-(trifluoromethyl)phenoxy]-3-(-22-thienyl)propanamine oxalate, mp =130° C.-131.5° C.

Analysis calculated for $C_{18}H_{20}F_3NO_5S$ Theory: C, 51.55; H, 4.81; N, 3.34; Found: C, 51.25; H, 4.91; N, 3.55.

EXAMPLE 19

N,N-Dimethyl-3-[4-(trifluoromethyl)phenoxy]-3-(3-thienyl)propanamine oxalate, mp =124° C.-125° C.

Analysis calculated $C_{18}H_{20}F_3NO_5S$ Theory: C, 51.55; H, 4.81; N, 3.34; Found: C, 51.35; H, 4.68; N, 3.39.

EXAMPLE 20

N-Methyl-3-[4-(trifluoromethyl)phenoxy-3-(2-thienyl)propanamine oxalate, mp =167° C.-168° C. dec.

Analysis calculated for $C_{17}H_{18}F_3NO_5S$ Theory: C, 50.37; H, 4.48; N, 3.46; Found: C, 50.40; H, 4.66; N, 3.72.

EXAMPLE 21

N,N-Dimethyl-3-[4-(trifluoromethyl)phenoxy]-3-(2-furanyl)propanamine, oil

Analysis calculated for $C_{16}H_{18}F_3NO_2$ Theory: C, 61.34; H, 5.79; N, 4.47; Found: C, 61.07; H, 5.82; N, 4.68.

EXAMPLE 22

N-Methyl-3-[4-(trifluoromethyl)phenoxy]-3-(3-thienyl)propanamine oxalate, mp =181° C.-182° C.

Analysis calculated for $C_{17}H_{18}F_3NO_5S$ Theory: C, 50.37; H, 4.48; N, 3.46; Found: C, 50.49; H, 4.42; N, 3.67.

EXAMPLE 23

N-Methyl-3-[4-(trifluoromethyl)phenoxy]-3-(2-furanyl)propanamine oxalate, mp =98° C.-102° C. dec.

15 Analysis calculated for $C_{17}H_{18}F_3NO_6$ Theory: C, 52.45; H, 4.66; N, 3.60; Found: C, 52.52; H, 4.45; N, 3.80.

EXAMPLE 24

N,N-Dimethyl-3-(4-methylphenoxy)-3-(2-thienyl)-propanamine oxalate, mp =132.5° C.-133.5° C.

Analysis calculated for $C_{18}H_{23}NO_5S$ Theory: C, 59.16; H, 6.34; N, 3.83; Found: C, 59.06; H, 6.12; N, 4.11.

EXAMPLE 25

N,N-Dimethyl-3-(4-chlorophenoxy)-3-(2-thienyl)-propanamine oxalate, mp =118° C.-119° C.

Analysis calculated for $C_{17}H_{20}ClNO_5S$ Theory: C, 52.95; H, 5.22; N, 3.63; Found: C, 52.85; H, 5.22; N, 3.48.

EXAMPLE 26

N-Methyl-3-(4-methylphenoxy)-3-(2-thienyl)-propanamine oxalate, mp =152° C.-153° C.

Analysis calculated for $C_{17}H_{21}NO_5S$ Theory: C, 58.10; H, 6.02; N, 3.99; Found C, 58.05; H, 6.04; N, 3.72.

EXAMPLE 27

N-Methyl-3-(4-chlorophenoxy)-3-(2-thienyl)-propanamine oxalate, mp =126° C.-129° C.

Analysis calculated for $C_{16}H_{18}ClNO_5S$ Theory: C, 51.68; H, 4.88; N, 3.77; Found: C, 51.60; H, 5.01; N, 3.52.

EXAMPLE 28

N-Methyl-3-(4-methoxyphenoxy)-3-(2-thienyl)-propanamine oxalate, mp =140° C.-143° C.

Analysis calculated for $C_{17}H_{21}NO_6S$ Theory: C, 55.57; H, 5.76; N, 3.81; Found: C, 55.31; H, 5.55; N, 4.06.

EXAMPLE 29

N,N-Dimethyl-3-(4-methoxyphenoxy)-3-(2thienyl)-propanamine oxalate, mp =110° C.-111.5° C.

Analysis calculated for $C_{18}H_{23}NO_6S$ Theory: C, 56.68; H, 6.08; N, 3.67; Found: C, 56.43; H, 5.85; N, 3.81.

EXAMPLE 30

N,N-Dimethyl-3-(1-naphthalenyloxy)-3-(2furanyl)-propanamine oxalate, mp =153° C.-155.5° C.

Analysis calculated for $C_{21}H_{23}NO_6$ Theory: C, 65.44; H, 6.02; N, 3.63; Found: C, 65.21; H, 5.75; N, 3.78.

EXAMPLE 31

N-Methyl-3-(1-naphthalenyloxy)-3-(2-furanyl)-propanamine oxalate, mp =145° C.-146° C.

Analysis calculated for $C_{20}H_{21}NO_6$ Theory: C, 64.68; H, 5.70; N, 3.77; Found: C, 64.79; H, 5.51; N, 3.95.

EXAMPLE 32

N,N-Dimethyl-3-(1-naphthalenyloxy)-3-(2thiazolyl)-propanamine oxalate, mp =190° C.-191° C. dec.

Analysis calculated for $C_{20}H_{22}N_2O_5S$ Theory: C, 59.69; H, 5.51; N, 6.96; Found: C, 59.99; H, 5.80; N, 7.01.

EXAMPLE 33

N,N-Dimethyl-3-(1-naphthalenyloxy)-3-(cyclohexyl)propanamine oxalate, mp =167° C.-169° C.

Analysis calculated for $C_{23}H_{31}NO_5$ Theory: C, 68.80; H, 7.78; N, 3.49; Found: C, 68.53; H, 7.53; N, 3.54.

EXAMPLE 34

N-Methyl-3-[4-(trifluoromethyl)phenoxy]-3(cyclohexyl)propanamine oxalate, mp =212° C.-213° C.

Analysis calculated for $C_{19}H_{26}F_3NO_5$ Theory: C, 56.29; H, 6.46; N, 3.45; Found: C, 56.19; H, 6.37; N, 3.32.

EXAMPLE 35

N,N-Dimethyl-3-[4-(trifluoromethyl)phenoxy]-3-(cyclohexyl)propanamine oxalate, mp =159° C.-160° C.

Analysis calculated for $C_{20}H_{28}F_3NO_5$ Theory: C, 57.27; H, 6.73; N, 3.34; Found: C, 57.49; H, 6.61; N, 3.20.

EXAMPLE 36

N-Methyl-3-(    -naphthalenyloxy)-3-(3-pyridyl)-propanamine oxalate, mp =98° C. dec.

Analysis calculated for $C_{21}H_{22}N_2O_5$ Theory: C, 65.96; H, 5.80; N, 7.33; Found: C, 64.27; H, 5.67; N, 7.01.

EXAMPLE 37

N,N-Dimethyl-3-(1-naphthalenyloxy)-3-(3-pyridyl)-propanamine oxalate, mp =176° C.-178° C.

Analysis calculated for $C_{22}H_{24}N_2O_5$ Theory: C, 66.65; H, 6.10; N, 7.07; Found: C, 66.53; H, 6.36; N, 6.41.

EXAMPLE 38

(+)-N-methyl-3-(1-naphthalenyloxy)-3-(2-thienyl)-propanamine oxalate, mp =133° C.-134° C.

Analysis calculated for $C_{20}H_{21}NO_5S$ Theory: C, 62.00; H, 5.46; N, 3.62; Found: C, 62.03; H, 5.51; N, 3.87.

EXAMPLE 39

(−)-N-methyl-3-(1-naphthalenyloxy)-3-(2-thienyl)-propanamine oxalate, mp =138° C.-138.5° C.

Analysis calculated for $C_{20}H_{21}NO_5S$ Theory: C, 62.00; H, 5.46; N, 3.62; Found: C, 61.72; H, 5.32; N, 3.82.

As noted above, the compounds of this invention are useful for inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

Compounds of the invention also have the ability to inhibit the uptake of norepinephrine. As such, yet another embodiment of this invention is a method for inhibiting norepinephrine uptake in mammals which comprises administering to a mammal requiring increased neurotransmission of norepinephrine a pharmaceutically effective amount of a compound of the invention.

The term "pharmaceutically effective amount", as used herein, represents an amount of a compound of the invention which is capable of inhibiting serotonin or norepinephrine uptake. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. The compounds of the invention unexpectedly inhibit the uptake of not only serotonin but also norepinephrine in mammals. It is a special feature of the compounds that they have good oral bioavailability without losing their substantial potent inhibiting effect of serotonin and norepinephrine uptake inhibiting effect. It is also a special feature of the compounds of the present invention in that they have been found to demonstrate a low degree of toxicity to mammals. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by brain serotoninengic and norepinephrinergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at rates set forth above for inhibiting serotonin and norepinephrine uptake in mammals.

The following experiment was conducted to demonstrate the ability of the compounds of the present invention to inhibit the uptake of serotonin and norepinephrine. This general procedure is set forth by Wong et al., in *Drug Development Research* 6:397–403 (1985).

Male Sprague-Dawley rats (110–150 g) from Harlan Industries (Cumberland, IN) were fed a Purina Chow ad libitum for at least 3 days before being used in the studies. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin($^3$H-5hydroxytryptamine, $^3$H-5HT) and $^{14}$C-l-norepinephrine ($^{14}$C-NE) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA, 50 nM $^3$H-5HT and 100 nM $^{14}$C-NE The reaction mixture was immediately diluted with 2 ml of ice-chilled Krebs-bicarbonate buffer and filtered under vacuum with a cell harvester (Brandel, Gaithersburg, MD). Filters were rinsed twice with approximately 5 ml of ice-chilled 0.9% saline and were transferred to a counting vial containing 10 ml of scintillation fluid (PCS, Amersham, Arlington Heights, IL). Radioactivity was measured by a liquid scintillation spectrophotometer. Accumulation of $^3$H-5HT and $^{14}$C-NE at 4° C. represented the background and was subtracted from all samples.

The results of the evaluation of various compounds of the present invention are set forth below in Table I. In the Table, columns 1–4 identify the structure of the compounds evaluated when taken with the formula set forth in the heading; column 5 identifies the salt form, if any, of the compound evaluated; and columns 6 and 7 provide the concentration of the test compound at $10^{-9}$M (nM) needed to inhibit 50% of serotonin (5HT) or norepinephrine, respectively, and is indicated in the Table as IC$_{50}$. The numbers in parentheses represent percent inhibition at 1000 nM.

TABLE I

INHIBITION OF 5HT AND NOREPINEPHRINE UPTAKE IN VITRO $$R^1-\underset{\underset{Ar}{\overset{|}{O}}}{\overset{|}{C}}HCH_2CH_2NR^2R^3$$

| Compound of Example No. | Ar | R$^1$ | R$^2$ | R$^3$ | Salt Form | IC$_{50}$(nM) 5HT | NE |
|---|---|---|---|---|---|---|---|
| 1 | 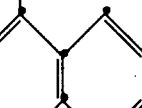 |  | CH$_3$ | CH$_3$ | oxalate | 13 | 600 |
| 2 | 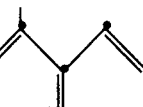 |  | CH$_3$ | H | oxalate | 17.5 | 38.5 |
| 3 |  |  | CH$_3$ | CH$_3$ | oxalate | 55 | 720 |
| 4 | 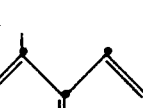 |  | CH$_3$ | CH$_3$ | oxalate | 76 | (41) |
| 5 |  |  | CH$_3$ | CH$_3$ | oxalate | 62 | 725 |

TABLE I-continued

INHIBITION OF 5HT AND NOREPINEPHRINE UPTAKE IN VITRO $$R^1-\underset{\underset{Ar}{\overset{|}{O}}}{CH}CH_2CH_2NR^2R^3$$

| Compound of Example No. | Ar | R¹ | R² | R³ | Salt Form | IC₅₀(nM) 5HT | IC₅₀(nM) NE |
|---|---|---|---|---|---|---|---|
| 6 | naphthyl, CF₃ | thienyl-CH₃ | CH₃ | CH₃ | oxalate | 114 | (9) |
| 7 | naphthyl, CF₃ | thienyl-CH₃ | CH₃ | H | oxalate | 95 | (46) |
| 8 | naphthyl | thienyl-CH₃ | CH₃ | CH₃ | oxalate | 25 | 630 |
| 9 | naphthyl | thienyl-CH₃ | CH₃ | H | oxalate | 18 | 69 |
| 10 | naphthyl, Cl | thienyl-CH₃ | CH₃ | CH₃ | oxalate | 36 | (31) |
| 11 | naphthyl, Cl | thienyl-CH₃ | CH₃ | H | oxalate | 49 | 77 |
| 12 | naphthyl, CH₃ | thienyl-CH₃ | CH₃ | CH₃ | oxalate | 58 | (40) |

TABLE I-continued
INHIBITION OF 5HT AND NOREPINEPHRINE UPTAKE IN VITRO $$R^1-CHCH_2CH_2NR^2R^3$$
$$|$$
$$O$$
$$|$$
$$Ar$$

| Compound of Example No. | Ar | R¹ | R² | R³ | Salt Form | IC₅₀(nM) 5HT | NE |
|---|---|---|---|---|---|---|---|
| 13 | 1-methylnaphthyl | 2-thienyl | CH₃ | H | maleate | 33 | 47 |
| 15 | naphthyl | tetrahydropyranyl | CH₃ | H | oxalate | 125 | 90 |
| 16 | naphthyl | thiazolyl | CH₃ | H | oxalate | 70 | 205 |
| 17 | 4-CF₃-phenyl | 2-furyl | CH₃ | CH₃ | oxalate | 210 | (5) |
| 18 | 4-CF₃-phenyl | 2-thienyl | CH₃ | CH₃ | oxalate | 190 | (15) |
| 19 | 4-CF₃-phenyl | 3-thienyl | CH₃ | CH₃ | oxalate | 125 | (17) |
| 20 | 4-CF₃-phenyl | 3-thienyl | CH₃ | H | oxalate | 46 | (52) |

TABLE I-continued

INHIBITION OF 5HT AND NOREPINEPHRINE UPTAKE IN VITRO $$R^1-CHCH_2CH_2NR^2R^3$$
$$|$$
$$O$$
$$Ar$$

| Compound of Example No. | Ar | R¹ | R² | R³ | Salt Form | IC₅₀(nM) 5HT | NE |
|---|---|---|---|---|---|---|---|
| 21 | 4-CF₃-phenyl | 2-furyl | CH₃ | CH₃ | | 140 | (14) |
| 22 | 4-CF₃-phenyl | 2-thienyl | CH₃ | H | oxalate | 100 | (36) |
| 23 | 3-CF₃-phenyl | 2-furyl | CH₃ | H | oxalate | 54 | 1100 |
| 24 | 3-CF₃-phenyl | 2-thienyl | CH₃ | CH₃ | oxalate | 125 | 430 |
| 25 | 4-Cl-phenyl | 2-thienyl | CH₃ | CH₃ | oxalate | 170 | 820 |
| 26 | 4-CH₃-phenyl | 2-thienyl | CH₃ | H | oxalate | 112 | 22 |

TABLE I-continued

INHIBITION OF 5HT AND NOREPINEPHRINE UPTAKE IN VITRO $$R^1-\underset{\underset{Ar}{O}}{C}HCH_2CH_2NR^2R^3$$

| Compound of Example No. | Ar | R¹ | R² | R³ | Salt Form | IC₅₀(nM) 5HT | NE |
|---|---|---|---|---|---|---|---|
| 27 | 4-Cl-phenyl | 2-thienyl | CH₃ | H | oxalate | 91 | 59 |
| 28 | 4-OCH₃-phenyl | 2-thienyl | CH₃ | H | oxalate | 50 | 260 |
| 29 | 4-OCH₃-phenyl | 2-thienyl | CH₃ | CH₃ | oxalate | 410 | (18) |
| 30 | 1-naphthyl | 2-furyl | CH₃ | CH₃ | oxalate | 11 | 30 |
| 31 | 1-naphthyl | 2-furyl | CH₃ | H | oxalate | 20 | 22.7 |
| 32 | 1-naphthyl | 2-thiazolyl | CH₃ | CH₃ | oxalate | 50 | 510 |
| 33 | 1-naphthyl | phenyl | CH₃ | CH₃ | oxalate | 210 | (47) |

TABLE I-continued

INHIBITION OF 5HT AND NOREPINEPHRINE UPTAKE IN VITRO

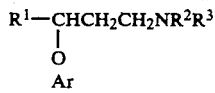

| Compound of Example No. | Ar | R¹ | R² | R³ | Salt Form | IC$_{50}$(nM) 5HT | NE |
|---|---|---|---|---|---|---|---|
| 34 | 4-CF₃-phenyl | cyclohexenyl | CH₃ | H | oxalate | 79 | 285 |
| 35 | 4-CF₃-phenyl | cyclohexenyl | CH₃ | CH₃ | oxalate | 260 | (21) |
| 36 | naphthyl | pyridyl | CH₃ | H | oxalate | 30 | 30 |
| 37 | naphthyl | pyridyl | CH₃ | CH₃ | oxalate | 315 | 315 |
| 38 | (+)-naphthyl | thienyl | CH₃ | H | oxalate | 12.3 | 38 |
| 39 | (−)-naphthyl | thienyl | CH₃ | H | oxalate | 21.5 | 34 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| (+)-N-methyl-3-(1-naphthalenyloxy)-3-(2-thienyl)propanamine maleate | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| N,N-dimethyl-3-(1-naphthalenyloxy)-3-(5-chloro-2-thienyl)propanamine oxalate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
|---|---|
| 3-(1-naphthalenyloxy)-3-(2-thiazoyl)propanamine hydrochloride | 0.25 |

-continued

|  | Weight % |
|---|---|
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

FORMULATION 4

Tablets each containing 60 mg of active ingredient are made as follows:

| N,N-dimethyl-3-[4-(trifluoromethyl)phenoxy]-3-(3-thienyl)propanamine oxalate | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| N,N-dimethyl-3-[4-(trifluoromethyl)phenoxy]-3-(2-furanyl)propanamine hydrobromide | 80 |
|---|---|
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient ma be made as follows:

| N-methyl-3-(2-naphthalenyloxy)-3-(2-thienyl)propanamine maleate | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| N,N-dimethyl-3-(4-chlorophenoxy)-3-(2-thienyl)propanamine succinate | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| | |
|---|---|
| N-methyl-3-(1-naphthalenyloxy)-3-(3-methyl-2-thienyl)propanamine acetate | 100 mg |
| isotonic saline | 1000 ml |

The solution of the above ingredients is administered intravenously at a rate of 1 ml per minute to a subject suffering from depression.

We claim:

1. A compound of the formula

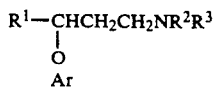

wherein:

$R^1$ is thienyl, halothienyl, ($C_1$-$C_4$ alkyl)thienyl, furanyl, pyridyl or thiazolyl;

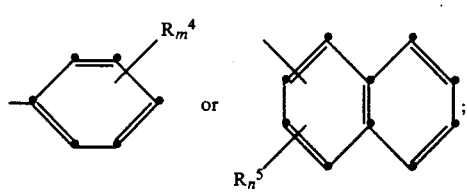

each of $R^2$ and $R^3$ independently is hydrogen or methyl;
each $R^4$ independently is halo, $C_1$-$C_4$ alkyl, $C_1$-$C_3$ alkoxy or trifluoromethyl;
each $R^5$ independently is halo, $C_1$C_4$ alkyl or trifluoromethyl;
m is 0, 1 or 2;
n is 0 or 1; and
the pharmaceutically acceptable acid addition salts thereof.

2. A compound of claim 1 wherein Ar is

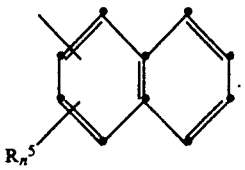

3. A compound of claim 2 wherein $R^1$ is halothienyl.
4. A compound of claim 2 wherein $R^1$ is ($C_1$-$C_4$ alkyl)thienyl.
5. A compound of claim 2 wherein $R^1$ is furanyl.
6. A compound of claim 2 wherein $R^1$ is pyridyl.
7. A compound of claim 2 wherein $R^1$ is thiazolyl.
8. A compound of claim 2 wherein $R^1$ is thienyl.
9. A compound of claim 8 wherein one of $R^2$ and $R^3$ is hydrogen and the other is methyl.
10. The compound of claim 10 which is N-methyl-3-(1-naphthalenyloxy)-3-(2-thienyl)propanamine, and its pharmaceutically acceptable acid addition salts.
11. The compound of claim 11 which is the (+) stereoisomer.
12. The compound of claim 12 which is (+)-N-methyl-3-(1-naphthalenyloxy)-3-(2-thienyl)propanamine maleate.
13. A compound of claim 1 wherein Ar is

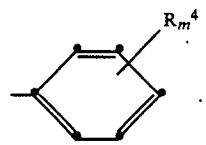

14. A compound of claim 13 wherein $R^1$ is thienyl.
15. A compound of claim 13 wherein $R^1$ is halothienyl.
16. A compound of claim 13 wherein $R^1$ is ($C_1$-$C_4$ alkyl)thienyl.
17. A compound of claim 13 wherein $R^1$ is furanyl.
18. A compound of claim 13 wherein $R^1$ is pyridyl.
19. A compound of claim 13 wherein $R^1$ is thiazolyl.
20. A method for inhibiting serotonin uptake in mammals which comprises administering to a mammal requiring increased neurotransmission of serotonin a pharmaceutically effective amount of a compound of claim 1.
21. A method of claim 20 wherein $R^1$ is thienyl.
22. A method of claim 21 wherein the compound is N-methyl-3-(1-naphthalenyloxy)-3-(2-thienyl)propanamine, and its pharmaceutically acceptable acid addition salts.
23. A method of claim 22 wherein the compound is (+)-N-methyl-3-(1-naphthalenyloxy)-3-(2-thienyl)-propanamine, and its pharmaceutically acceptable acid addition salts.
24. A method for inhibiting norepinephrine uptake in mammals which comprises administering to a mammal requiring increased neurotransmission of norepinephrine a pharmaceutically effective amount of a compound of claim 1.
25. A method of claim 24 wherein one of $R^2$ and $R^3$ is hydrogen and the other is methyl.
26. A method of claim 25 wherein the compound is N-methyl-3-(1-naphthalenyloxy)-3-(2-thienyl)propanamine, and its pharmaceutically acceptable acid addition salts.

27. A method of claim 25 wherein the compound is (+)-N-methyl-3-(1-naphthalenyloxy)-3-(2-thienyl)propanamine, and its pharmaceutically acceptable acid addition salts.

28. A method of treating depression in humans comprising administering to a human suffering from depression an effective antidepressant dose of a compound of claim 1.

29. A method claim 28 wherein R¹ is thienyl.

30. A method of claim 29 wherein the compound is N-methyl-3-(1-naphthalenyloxy)-3-(2-thienyl)propanamine, and its pharmaceutically acceptable acid addition salts.

31. A method of claim 30 wherein the compound is (+)-N-methyl-3-(1-naphthalenyloxy)-3-(2-thienyl)propanamine, and its pharmaceutically acceptable acid addition salts.

32. A method of treating anxiety in human comprising administering to a human suffering from anxiety an effective antianxiety dose of a compound of claim 1.

33. A method of claim 32 wherein R¹ is thienyl.

34. A method of claim 33 wherein the compound is N-methyl-3-(1-naphthalenyloxy)-3-(2-thienyl)propanamine, and its pharmaceutically acceptable acid addition salts.

35. A method of claim 34 wherein the compound is (+)-N-methyl-3-(1-naphthalenyloxy)-3-(2-thienyl)propanamine, and its pharmaceutically acceptable acid addition salts.

36. A method of treating obesity in humans comprising administering to a human suffering from obesity an effective antiobesity dose of a compound of claim 1.

37. A method of claim 38 wherein R¹ is thienyl.

38. A method of claim 37 wherein the compound is N-methyl-3-(1-naphthalenyloxy)-3-(2-thienyl)propanamine, and its pharmaceutically acceptable acid addition salts.

39. A method of claim 38 wherein the compound is (+)-N-methyl-3-(1-naphthalenyloxy)-3-(2-thienyl)propanamine, and its pharmaceutically acceptable acid addition salts.

40. A method of suppressing the desire of humans to smoke comprising administering to a human in need of such suppression an effective dose to relieve the desire to smoke of a compound of claim 1.

41. A method of claim 40 wherein R¹ is thienyl.

42. A method of claim 41 wherein the compound is N-methyl-3-(1-naphthalenyloxy)-3-(2-thienyl)propanamine, and its pharmaceutically acceptable acid addition salts.

43. A method of claim 42 wherein the compound is (+)-N-methyl-3-(1-naphthalenyloxy)-3-(2-thienyl)propanamine, and its pharmaceutically acceptable acid addition salts.

44. A method of suppressing the desire of humans to consume alcohol comprising administering to a human in need of such suppression an effective dose to relieve the desire to consume alcohol of a compound of claim 1.

45. A method of claim 44 wherein R¹ is thienyl.

46. A method of claim 45 wherein the compound is N-methyl-3-(1-naphthalenyloxy)-3-2-thienyl)propanamine, and its pharmaceutically acceptable acid addition salts.

47. A method of claim 46 wherein the compound is (+)-N-methyl-3-(1-naphthalenyloxy)-3-(2-thienyl)propanamine, and its pharmaceutically acceptable acid addition salts.

48. A pharmaceutical formulation comprising a compound of claim 1 and a pharmaceutically acceptable carrier, diluent or excipient therefor.

49. A formulation of claim 48 wherein R¹ is thienyl.

50. A formulation of claim 49 wherein the compound is N-methyl-3-(1-naphthalenyloxy)-3-(2-thienyl)propanamine, and its pharmaceutically acceptable acid addition salts.

51. A formulation of claim 50 wherein the compound is (+)-N-methyl-3-(1-naphthalenyloxy)-3-(2-thienyl)propanamine, and its pharmaceutically acceptable acid.

* * * * *

UNITED STATES PATENT AND TRADEMARK OFFICE
CERTIFICATE OF CORRECTION

PATENT NO. : 5,023,269

DATED : June 11, 1991

INVENTOR(S) : Joseph H. Krushinski, Jr., David W. Robertson, and David T. Wong

It is certified that error appears in the above-identified patent and that said Letters Patent is hereby corrected as shown below:

Column 1, line 40, insert "Ar is" after "thiazolyl;"
Column 2, line 23, change "$C_1-C_4$ alkyl)thienyl" to -- ($C_1-C_4$ alkyl)thienyl --
Column 3, line 49, change "N-Methyl-3-(4-met naphthalenyloxy)-" to -- N-Methyl-3-(4-methyl-1-naphthalenyloxy)- --
Column 3, line 53, change "N,N-Dimethyl-3-6-" to -- N,N-Dimethyl-3-(6- --
Column 4, line 35, change "3-4-(Trifluoromethyl)phenoxy" to -- 3-[4-(Trifluoromethyl)phenoxy --
Column 6, line 30, change "$C_0H_{14}ClNOS$" to -- $C_9H_{14}ClNOS$ --
Column 6, line 34, change "(2-thenyl)" to -- (2-thienyl) --
Column 6, line 49, change "$C_9H_{19}NOS$" to -- $C_9H_{15}NOS$ --
Column 8, line 51, change "42.S3" to -- 42.53 --
Column 9, line 17, change "S6.04" to -- 56.04 --
Column 9, line 52, change "S8.34" to -- 58.34 --
Column 11, line 37, change "b4.49" to -- 64.49 --
Column 13, line 5, change "(2thienyl)-" to -- (2-thienyl) --
Column 13, line 23, change "(2thiazolyl)-" to -- (2-thiazolyl) --
Column 13, line 47, change "N-Methyl-3-( -naphthalenyloxy)" to -- N-Methyl-3-(1-naphthalenyloxy) --
Column 29, line 55, insert "Ar is" after "thiazolyl;"
Column 29, line 63, change "$C_1C_4$" to -- $C_1-C_4$ --
Column 30, line 20, change "claim 10" to -- claim 9 --
Column 30, line 23, change "claim 11" to -- claim 10 --
Column 30, line 25, change "claim 12" to -- claim 11 --

UNITED STATES PATENT AND TRADEMARK OFFICE
CERTIFICATE OF CORRECTION

PATENT NO. : 5,023,269

DATED : June 11, 1991

INVENTOR(S) : Joseph H. Krushinski, Jr., et al.

It is certified that error appears in the above-identified patent and that said Letters Patent is hereby corrected as shown below:

Column 31, line 35, change "claim 38" to -- claim 36 --.

Signed and Sealed this

Tenth Day of November, 1992

Attest:

DOUGLAS B. COMER

*Attesting Officer*   *Acting Commissioner of Patents and Trademarks*